United States Patent [19]
Imran et al.

[11] Patent Number: 5,536,252
[45] Date of Patent: Jul. 16, 1996

[54] ANGIOPLASTY CATHETER WITH MULTIPLE COAXIAL BALLOONS

[75] Inventors: Mir A. Imran, Palo Alto; Deepak R. Gandhi, San Jose, both of Calif.

[73] Assignee: Intelliwire, Inc., Sunnyvale, Calif.

[21] Appl. No.: 331,219

[22] Filed: Oct. 28, 1994

[51] Int. Cl.⁶ .................................................. A61M 29/00
[52] U.S. Cl. ............................ 604/101; 604/96; 606/194
[58] Field of Search ............................ 604/96, 101, 102, 604/97; 606/192, 194, 195

[56] References Cited

U.S. PATENT DOCUMENTS

| | | | |
|---|---|---|---|
| 4,423,725 | 1/1984 | Baran et al. | 604/101 X |
| 4,744,366 | 5/1988 | Jang | 128/344 |
| 4,763,654 | 8/1988 | Jang | 128/344 |
| 4,990,139 | 2/1991 | Jang | 604/101 |
| 4,994,033 | 2/1991 | Shockey et al. | 604/101 |
| 5,049,132 | 9/1991 | Shaffer et al. | 604/101 |
| 5,213,576 | 5/1993 | Abiuso et al. | 604/96 |

*Primary Examiner*—Corrine M. McDermott
*Attorney, Agent, or Firm*—Flehr, Hohbach, Test, Albritton & Herbert

[57] ABSTRACT

An angioplasty catheter comprising a flexible elongate tubular member having proximal and distal extremities. A lumen therein extends from the proximal extremity to the distal extremity. First and second balloons are carried by said distal extremity and are coaxially disposed with respect to each other on the distal extremity of the flexible elongate tubular member. Means are carried by the flexible elongate tubular member for inflating the first and second balloons one at a time independent of each other.

17 Claims, 3 Drawing Sheets

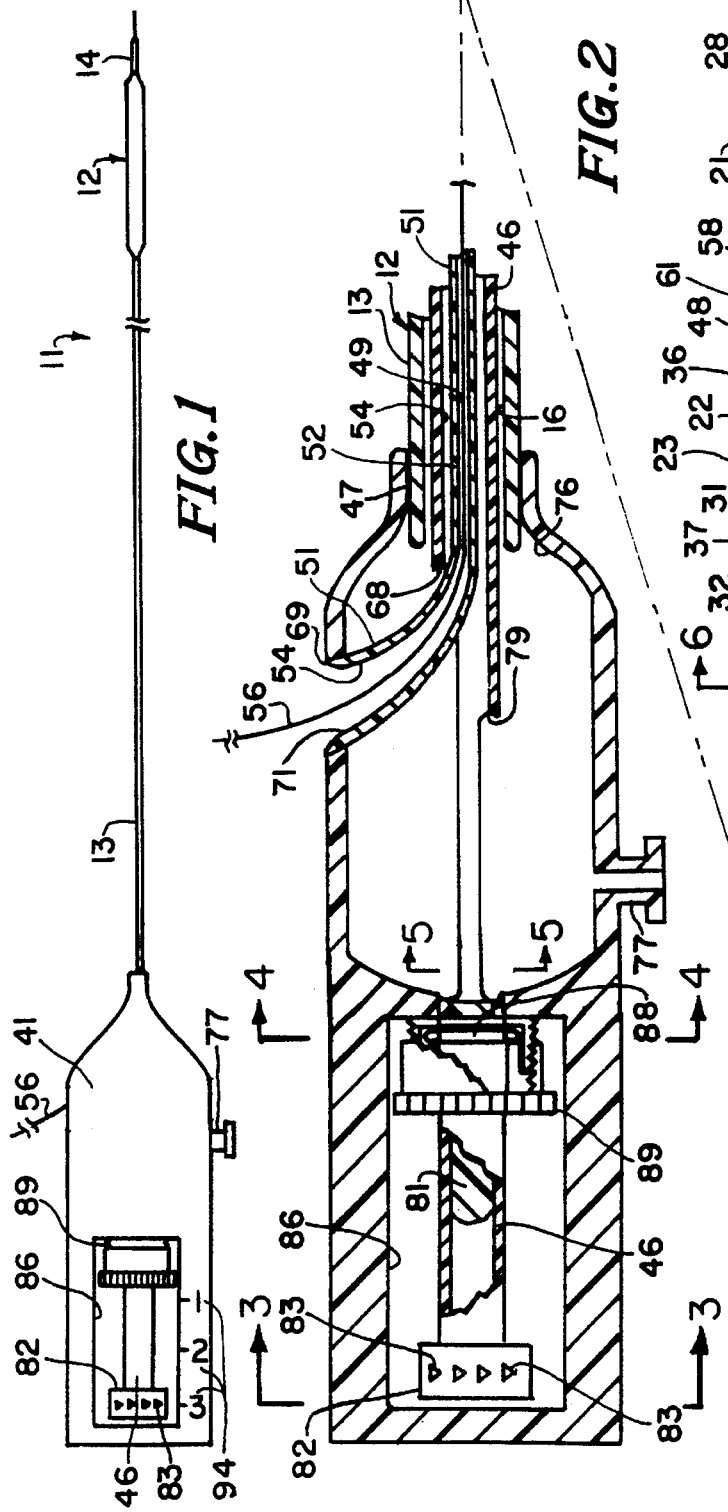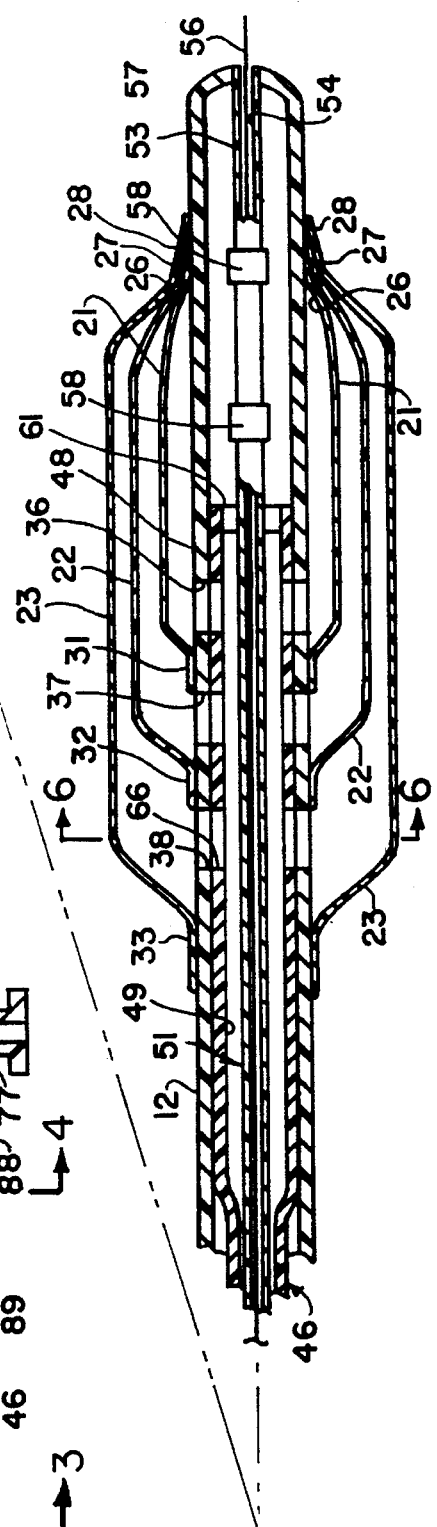

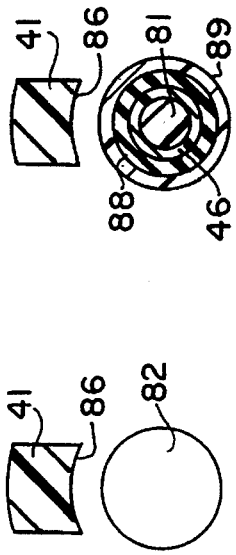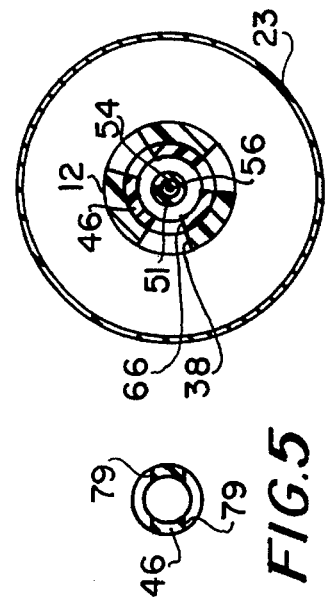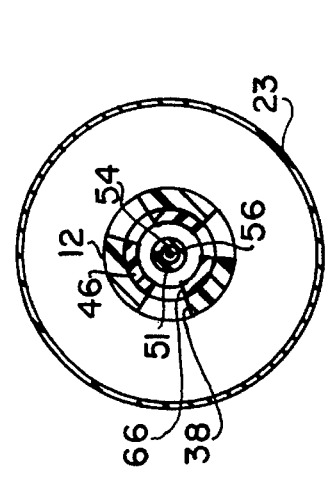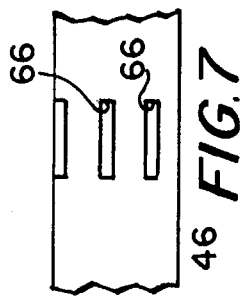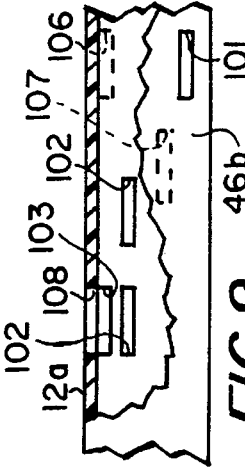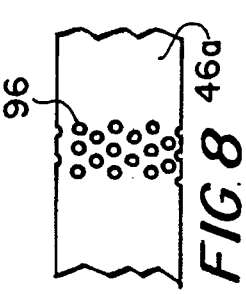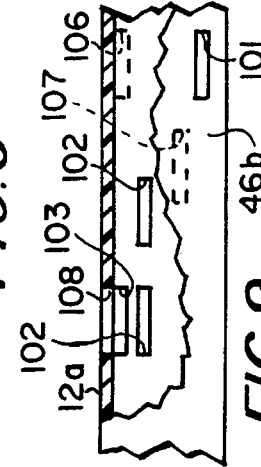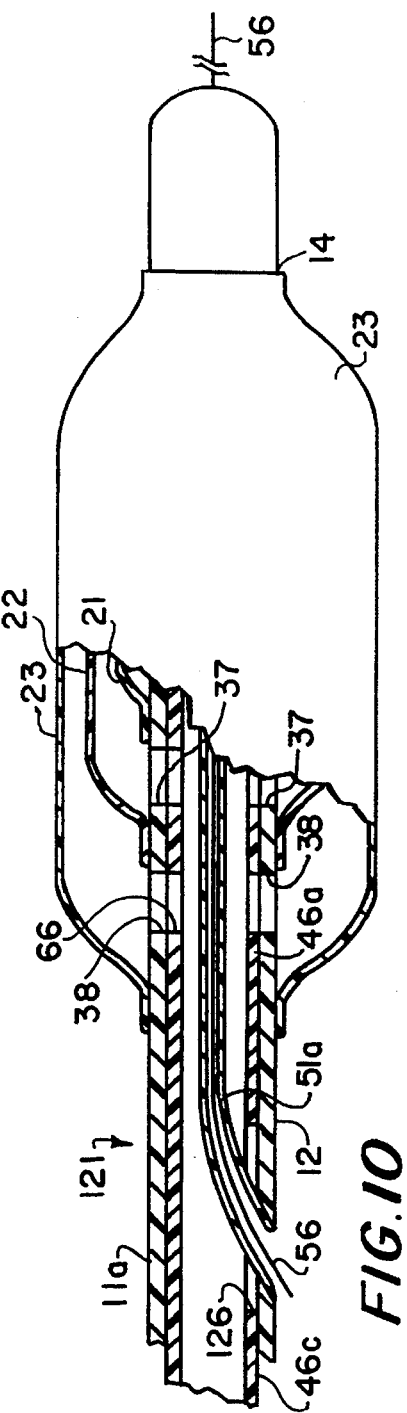

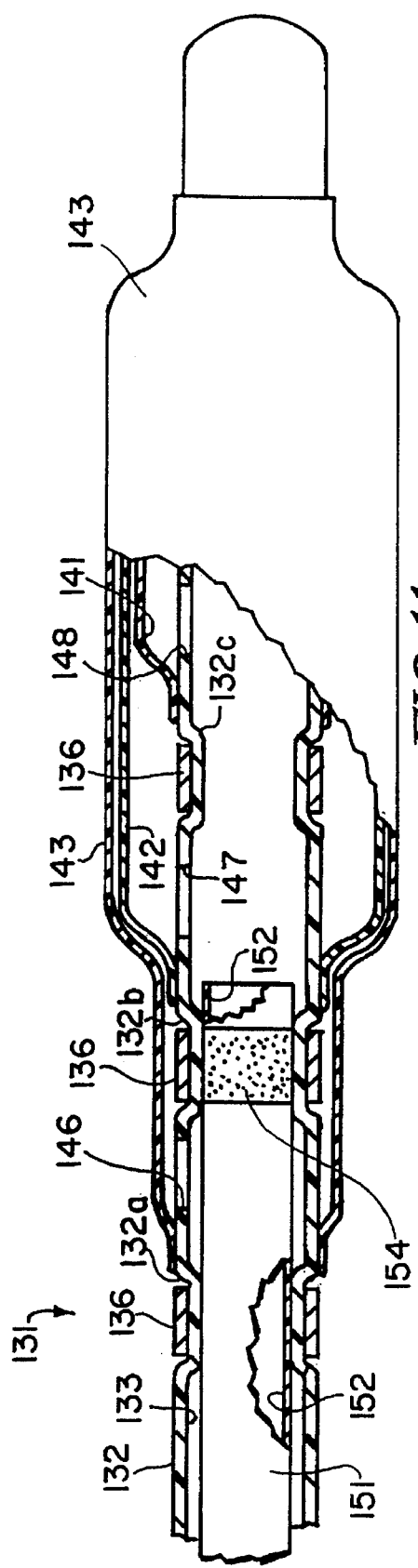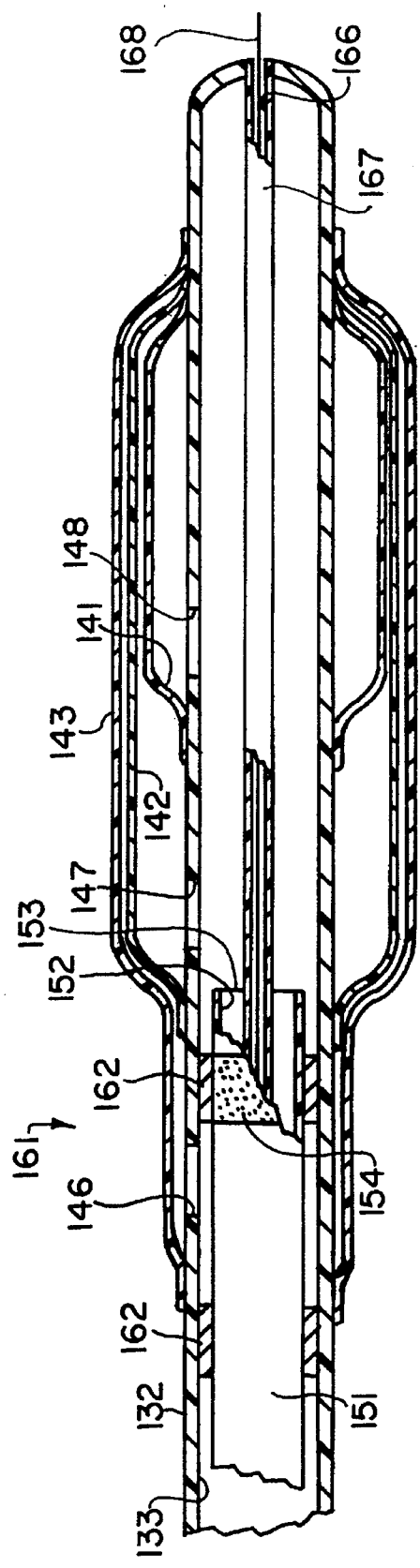

ANGIOPLASTY CATHETER WITH MULTIPLE COAXIAL BALLOONS

This invention relates to an angioplasty catheter with multiple coaxial balloons.

Angioplasty catheters heretofore have been provided. In many angioplasty procedures, it has been found that it is necessary to use more than one angioplasty balloon catheter because it is the practice to start with a small balloon angioplasty catheter as for example a two millimeter balloon and to remove that angioplasty balloon catheter and go to one or more larger sized angioplasty balloon catheters. Thus, statistically it has been found that on average approximately 2½ balloon catheters are used per angioplasty procedure. In connection with the use of such different sized balloons, typically it has been necessary to withdraw one angioplasty catheter and substitute another as for example one with a larger sized balloon. Attempts have been made to solve this problem by utilizing an angioplasty catheter having tandem balloons in which different-sized balloons are spaced longitudinally of the catheter in which a separate balloon lumen is provided for inflating each balloon. This has been found to be unsatisfactory because if the proximal balloon is being used, the distal non-active portion of the catheter must be advanced further down into the coronary artery which may be undesirable. There is therefore need for a new and improved angioplasty catheter which can overcome these difficulties.

In general, it is obvious to the present invention to provide an angioplasty catheter with multiple coaxial balloons.

The object of the invention is to provide a catheter of the above character in which the balloons can be successively inflated.

Another object of the invention is to provide a catheter of the above character which can be rapidly exchanged if desired.

Additional objects and features of the invention will appear from the following description in which the preferred embodiments are set forth in detail in conjunction with the accompanying drawings.

FIG. 1 is a side elevational view of an angioplasty catheter incorporating the present invention.

FIG. 2 is an enlarged sectional view of the angioplasty catheter shown in FIG. 1.

FIG. 3 is a cross sectional view taken along the line 3—3 of FIG. 2.

FIG. 4 is a cross sectional view taken along the line 4—4 of FIG. 2.

FIG. 5 is a cross sectional view taken along the line 5—5 of FIG. 2.

FIG. 6 is a cross sectional view taken along the line 6—6 of FIG. 2.

FIG. 7 is a partial side elevational view showing the slidable member for successively inflating the balloons incorporating the present invention.

FIG. 8 is a partial side elevational view showing another embodiment of a slider tube incorporating the present invention.

FIG. 9 is a partial side elevational view of still another embodiment of a slider tube for use in the angioplasty catheter incorporating the present invention.

FIG. 10 is a partial sectional view of another embodiment of an angioplasty catheter for rapid exchange incorporating the present invention.

FIG. 11 is a side elevational view in section showing another embodiment of an angioplasty catheter incorporating the present invention.

FIG. 12 is a side elevational view in section similar to that shown in FIG. 11 but showing still another embodiment of an angioplasty catheter incorporating the present invention.

In general, the angioplasty catheter of the present invention is comprised of a flexible elongate tubular member having proximal and distal extremities and having a lumen therein extending from the proximal extremity to the distal extremity. At least first and second balloons are carried by the distal extremity and are coaxially disposed with respect to each other. Means is carried by the tubular member for successively inflating the first and second balloons.

More in particular as shown in FIGS. 1 through 7 of the drawings, the angioplasty catheter 11 incorporating the present invention consists of a flexible elongate tubular member 12 formed of a suitable medical grade plastic having proximal and distal extremities 13 and 14 and having a lumen 16 extending from the proximal extremity to the distal extremity 14.

By way of example the flexible elongate tubular member 12 can be of a suitable size as for example 3½ French which corresponds to an outside diameter of 0.045". The lumen 16 has a diameter of 0.037" to provide a wall thickness for the flexible elongate member 12 of 0.004".

A plurality of balloons, as for example three balloons as shown in FIG. 2, are provided in which a small size balloon 21 is mounted on the distal extremity 14 of the flexible elongate tubular member 12. Over the small size balloon 21 an intermediate size balloon 22 is coaxially mounted on the distal extremity 14. A large size balloon 23 is coaxially mounted over the intermediate size balloon 22 and over the small size balloon 21. The distal extremities 26, 27 and 28 of the balloons 21, 22 and 23 generally overlie each other as shown in FIG. 2 and are bonded to the distal extremity 14 of the flexible elongate number 12 by suitable means such as an adhesive to form fluid-tight seals between the exterior surface of the flexible elongate member 12 and the distal extremities 26, 27 and 28 of the balloons 21, 22 and 23.

The proximal extremities 31, 32 and 33 of the balloons 21, 22 and 23 are secured to the flexible elongate member 12 proximal of the region in which the distal extremities 26, 27 and 28 are adhered to the distal extremity of the flexible elongate tubular member 12. For coronary applications, the balloon 21 can be sized to have an outside diameter of 1.5 to 2.0 millimeters. The medium size balloon 22 can have a maximum inflatable diameter of 2.0 to 2.75 millimeters and the large size balloon 23 can have a maximum inflated outside diameter of 2.75 to 4.00 millimeters. For peripheral applications and other applications, the sizes can be increased or decreased as desired. The proximal extremities 31, 32 and 33 are staggered with respect to each other longitudinally of the flexible elongate tubular member as shown particularly in FIG. 2. This makes it possible to accommodate inflation slots 36, 37 and 38 which are provided in the side wall of the flexible elongate tubular member 12 that are in communication respectively with the balloons 21, 22 and 23 and with the central lumen 16.

A handle 41 is mounted on the proximal extremity 13 of the flexible elongate tubular member 12. It can be formed of a suitable moldable plastic such as Ultem. It has a length and diameter so that it can be readily grasped by the human hand as for example it can have a length of 4" and a width of 1". The handle 41 can be molded onto the proximal extremity 13 of the flexible elongate member 12 or alternatively can be secured thereto by suitable means such as an adhesive.

A slidable valve tube of 46 is slidably mounted within the lumen 16 of the flexible elongate tubular member 12 and has proximal and distal extremities 47 and 48. The valve tube 46 has a lumen 49 extending from the proximal extremity to the distal extremity. The valve tube can have a suitable wall thickness as for example 0.005". The valve tube 46 is formed of a suitable plastic material such as polyamide or polyethylene. It is desirable that the distal extremity 48 be made of material which is at least partially elastic so that it can be expanded into intimate contact with the inner surface forming the lumen 16 of the flexible elongate member 12 to form a fluid tight seal therewith for inflating the balloons 21, 22 and 23 as hereinafter described. Thus, although the distal extremity 48 should be relative elastic and soft, the remainder of the valve tube 46 should be of a higher durometer material. As shown the portion of the valve tube 46 proximal of the distal extremity 48 can be of a reduced diameter so that the friction between the valve tube 46 and the inner surface of the flexible elongate tubular member 12 forming the lumen 16 is reduced. In addition, the exterior surface of the valve tube 46 proximal of the distal extremity 48 can be provided with a lubricous coating as for example silicone to further reduce the friction between the valve tube 46 and the flexible elongate tubular member 12.

A guide wire or tubular member 51 is disposed within the valve tube 46 and is provided with proximal and distal extremities 52 and 53. A lumen 54 extends from the proximal extremity 52 to the distal extremity 53 of the tubular member 51. The guide wire or tubular member 51 also can be formed of suitable material such as a polyimide. It can have a suitable outside diameter of, for example 0.023" can have a wall thickness of 0.002" to provide a lumen 54 having a diameter of 0.019" so that guide wires of various sizes as for example a guide wire 56 having an outside diameter of 0.014" can be readily introduced therethrough. The distal extremity 53 of the guide wire or tubular member 51 is bonded to the distal extremity of the flexible elongate tubular member 12 to form a liquid fluid tight seal therebetween and at the same time to form a rounded distal extremity for the flexible elongate tubular member 12 to provide a rounded hemispheric surface 57.

A pair of radiopaque longitudinally spaced apart markers 58 is provided on the exterior surface of the guide wire or tubular member 51 with one of the markers 58 being disposed at the commencement of the inflatable distal portions of the balloons 21, 22 and 23 and the other marker 58 being disposed generally at midpoint between the ends of the small size balloon 21 as shown in FIG. 2.

Means is provided for forming a fluid-tight seal between the distal extremity 48 of the valve tube 46 and the distal extremity 53 of the guide wire or tubular member 51 which consists of a resilient seal 61 formed of a suitable material such as an elastomer to provide a fluid-tight seal with respect to the guide wire or tubular member 51 while permitting slidable movement of the valve tube 46 with respect thereto.

Means is provided for providing communication between the lumen 49 in the valve tube 46 and successively one by one of the slots 36, 37 and 38 provided in the flexible elongate tubular member 12. Such means as shown in FIGS. 2, 6 and 7 consists of a plurality of circumferentially aligned spaced-apart slots 66 provided in the slidable valve tube 46. By way of example three of such slots 66 have been provided which are spaced 120° and which have suitable length as for example 0.25" and a width of 0.10".

The proximal extremity 52 of the guide wire or tubular member 51 extends through an elongate slot 68 provided in the proximal extremity 47 of the valve tube 46. The proximal extremity 52 is outwardly flared and is bonded into a hole 69 provided in the handle 41 by suitable means such an adhesive (not shown) to provide an opening 71 providing an entrance into the lumen 54. The material forming the guide wire or tubular member 51 can be relatively flexible so that it can accommodate the slidable movement of the valve tube 46 as hereinafter described.

The handle 41 is provided with an enclosed fluid-tight chamber 76. A conventional Luer-type fitting 77 is mounted in the housing and is in communication with the chamber 76 for providing a fluid for filling of the balloons 21, 22 and 23 as hereinafter described. Means is provided for establishing communication between the chamber 76 and the lumen 49 provided in the slidable valve tube 46 and consists of a pair of opposed elongate longitudinally extending slots 79 provided in the valve tube 46 which are in communication with the lumen 49.

The proximal extremity of the valve tube 46 is provided with a solid portion 81 proximal of the slot 79 and has a knob 82 which has a cylindrical configuration and which is provided with indicia 83 on the outer surface thereof which are in the form of small triangles which are spaced apart circumferentially with their apexes facing in the same clockwise direction as viewed from the proximal end. The knob 82 is disposed in a rectangular recess 86 provided in the handle 41 and is movable longitudinally of the recess 86 to move the valve tube 46 axially and longitudinally of the lumen 16 to move the slots 66 into registration selectively one at a time with the set of slots 36, 37 and 38.

Sealing means is provided for establishing a sealing engagement with respect to the slidable valve tube 46 and the body forming the handle 41 and consists of an O-ring 88 retained within an adjustable collet 89 which threadably engages the solid portion 81 of the valve tube 46 for establishing a fluid tight seal between the solid portion 81 of the slidable valve tube 46 and the body forming the handle 41. The collet 89 is accessible through the opening 86 so that it can be adjusted to compress an o-ring seal 88 to obtain a fluid tight seal while still permitting linear motion of the valve tube 46. The O-ring seal 88 can also be utilized to permit rotation of the knob 82 and the valve tube 46 as hereinafter described.

As shown particularly in FIG. 1, the body or handle 41 is provided with indicia 94 in the form of the numerals 1, 2 and 3. These indicia 94 are adapted to be utilized in connection with indicia 83 on the knob 82 during rectilinear movement within the rectangular recess 86 to select the balloons 21, 22 and 23 to be inflated, with the number "1" indicating the small size balloon 21, number "2" indicating the medium size balloon 22, and number "3" indicating the large size balloon 23.

Operation and use of the angioplasty catheter 11 shown in FIGS. 1 through 7 of the drawings may now be briefly described as follows. Let it be assumed that the catheter has been provided with a small balloon 21 having a maximum inflated diameter of 1.75 millimeters, the middle balloon having a maximum inflated diameter of 2.25 millimeters and the largest balloon 23 having a maximum inflated outside diameter 3.0 millimeters. At the time of the commencement of the angioplasty procedure, the balloons 21, 22 and 23 are all deflated so that the outside diameter of the flexible elongate tubular member 12 is only increased by the wall thicknesses of the three deflated balloons which are coaxially mounted thereon.

In the angioplasty procedure, a guiding catheter (not shown) can be inserted into the femoral artery and is deployed in a manner well known to those skilled in the art. Thereafter, a guide wire 56 can be positioned within the lumen 54 of the tubular member 51 by introducing the distal extremity of the guide wire 56 through the opening 71 of the catheter 11 and through the lumen 54 until it extends beyond the distal extremity of the flexible elongate tubular member 12 as shown in FIG. 2. The catheter 11 with the guide wire 56 therein can then be introduced into the guiding catheter with the guide wire 56 being advanced into the vessel of the patient ahead of the catheter 11. Let it be assumed that the guide wire 56 of a conventional type has been advanced through a stenosis in a vessel in a patient in which it is desired to perform an angioplasty procedure. As soon as the guide wire 56 has been passed through the stenosis, the catheter 11 can be passed over the guide wire to follow the guide wire until the balloons 21, 22 and 23 are in registration with the stenosis. This movement can be observed by observing the positioning of the radiopaque markers 58.

As soon as the balloons 21, 22 and 23 are in registration within the stenosis, the physician doing the procedure typically will utilize the small balloon 21 first. This is accomplished by moving the knob 82 until the registration indicia 83 carried by the knob 82 are in registration with the number "1" of the indicia 94 carried by the body 41. When this is the case, the slots 66 are in engagement with the slots 36 and the small inelastic balloon 21 is inflated by introducing an inflatable fluid as for example a radiopaque dye or a saline solution into a fitting 77 in a conventional manner to inflate the chamber 76 to cause the fluid to pass through the slots 79 into the lumen 49 and then through the slots 66 and through the slots 36 in the flexible elongate member 12 to inflate the small size balloon 21. As this occurs, the walls forming the balloons 22 and 23 will be moved outwardly in conjoint movement with the wall of the inner balloon 21 to cause dilation of the stenosis in which the balloons 21, 22 and 23 are disposed in a manner well known to those skilled in the art. After the balloon 21 has been inflated once or possibly several times to accomplish the desired dilation of the stenosis, the physician can retract the catheter so that the balloons 21, 22 and 23 are moved out of the stenosis while leaving the guide wire in place to ascertain whether or not adequate blood flow has been established through the dilated stenosis.

Let it be assumed that the desired blood flow has not been obtained and it is desired to utilize the next larger or mid-size balloon 22. The distal extremity of the catheter 11 can then be again positioned within the stenosis by moving it distally over the guide wire 56 which is still in place until the balloon 22 is in registration with the stenosis. The knob 82 is then pulled proximally so that the indicia 83 are in registration with the number "2" of the indicia 94 carried by the handle 41 bringing the slots 66 into engagement and in registration with the slots 37 in the inner flexible elongate tubular member 12. Thereafter, the intermediate sized balloon 22 can be inflated at the same time that the inner or small balloon 21 is inflated by introducing an inflation fluid through the fitting 77. Inflation of the small balloon 21 does not affect inflation of the balloon 22 because it is of a smaller size. The outer or larger balloon 23 since it is not being inflated will be moved outwardly by the force of the intermediate balloon 22 and thus the size of the intermediate balloon 22 is only increased by the wall thickness of the outer or larger balloon 23. This will cause the stenosis to be enlarged under the force of the intermediate balloon 22 to a size corresponding to the intermediate balloon 22. After the balloon 22 has been inflated one or more times, the catheter 11 can be pulled proximally so that it clears the stenosis while leaving the guide wire 56 in place. Blood flow measurements passing through the stenosis can then be made.

If it is determined that the blood flow is still inadequate, the balloon catheter 11 can be readvanced over the guide wire 56 into the stenosis so that the larger balloon 23 is in registration with the stenosis. The valve tube 46 is then retracted by use of the knob 82 until the indicia 83 are in registration with the number "3" of the indicia 94 on the handle 41. Thereafter, the inflation fluid can be introduced through the fitting 77 to cause inflation of the largest balloon 23 as well as balloons 22 and 21. Inflation of the balloons 22 and 21 does not affect inflation of the largest balloon 23 because of their smaller sizes. The large size balloon 23 can be inflated and deflated one or more times as desired by the physician to cause a still further expansion or dilation of the stenosis.

After it has been ascertained by the physician that a successful angioplasty procedure has been performed by measuring the blood flow through the stenosis, the catheter 11 along with the guide wire 56 can be removed along with the guide tube in a manner known well to those skilled in the art.

From the foregoing it can be seen that with multiple coaxially mounted balloons it is possible to select any one of a number of different diameter balloons to achieve the appropriate dilation of the stenosis in a vessel in the human body. This makes is unnecessary to withdraw the catheter from the body and insert a new catheter as has been the practice in the past. Different size balloons can be selected for performing the angioplasty even while the catheter is disposed within the stenosis. Also as hereinbefore described, the procedure can be performed with one of the balloons and a blood flow check can thereafter be made. Other balloons can be utilized as desired until the range of the balloon sizes provided on the catheter tip has been exhausted.

Another embodiment of the catheter 11 of the present invention as can be seen from FIG. 8 can replace the elongate slots 66 with a plurality of perforations 96 arranged in a circumferential band on the valve tube 46a. As with the slots 66, these perforations 96 can be moved selectively into engagement with the slots 36, 37 and 38 in the manner hereinbefore described.

In FIG. 9, there is shown another embodiment of the invention in which a valve tube 46b is provided with a plurality of slots 101, 102 and 103. By way of example there can be provided three of such slots 101 which are spaced 120° apart and similarly three slots 102 can be provided which are offset by suitable angles as for example 40° with respect to the slots 101 and similarly three circumferentially spaced apart slots 103 can be provided which are offset by 40° with respect to the slots 102. These slots 101, 102 and 103 can be moved by rotation of the valve tube 46b into registration with corresponding range slots 106, 107 and 108 provided in the flexible elongate member 12a for inflating the balloons 21, 22 and 23 in the manner hereinbefore described.

It should be appreciated that in place of the movable guide wire 56 shown in the embodiment of the invention in FIGS. 1–7 that the guide wire or tubular member 51 can be eliminated and a fixed guide wire (not shown) can be substituted for the movable guide wire 56. The fixed guide wire can be in the form of a coil spring secured to the rounded tip providing the surface 57. Utilization of a fixed guide wire makes it possible to reduce the diameter of the catheter 11.

Another embodiment of the invention is shown in FIG. 10 in which the catheter 121 can be used with a rapid exchange system of a type well known to those skilled in the art. In this embodiment of the invention, the catheter is constructed in the same manner as hereinbefore described with the exception that the guide wire or tubular member 51a is brought out near the distal extremity of the catheter 11 as shown in FIG. 10. The valve tube 46c is provided with an elongate slot 126 to accommodate the guide wire or tubular member 51 during slidable movement of the valve tube 46c in the manner hereinbefore described. Utilizing such a construction, the catheter of the present invention can be substituted in a rapid exchange for another catheter which has been constructed to be utilized in connection with a rapid exchange system.

In FIG. 11, there is shown another embodiment of an angioplasty catheter 131 which has been provided with multiple coaxial balloons incorporating the present invention. The angioplasty catheter 131 is comprised of a flexible elongate member 132 formed of a medical grade plastic which is provided within the lumen 133 extending therethrough. The flexible elongate tubular member 132 in accordance with the present invention is provided with necked down annular portions 132a, 132b and 132c which are spaced apart longitudinally of the distal extremity of the flexible elongate tubular member 132. In order to ensure that the necked down portions 132a, 132b and 132c remain in the elongate tubular member 132, bands 136 of a suitable radiopaque material such as platinum can be disposed within the necked down portions 132a, 132b and 132c as shown.

As in the previous embodiments, a plurality of coaxially mounted balloons, as for example three, which can be identified as small, medium and large balloons 141, 142 and 143, respectively are mounted on the distal extremity of the elongate tubular member 132. As in the previous embodiments, the balloons 141, 142 and 143 have their distal extremities bonded by a fluid tight seal to the exterior surface of the flexible elongate tubular member 132. The proximal extremities of balloons 142 and 143 are also bonded with adhesive fluid tight seals to the flexible elongate tubular member 132 in the regions immediately distal to the portions 132a, 132b and 132c as shown so that the interiors of the balloons 141, 142 and 143 are open respectively to openings 146, 147 and 148 leading into the lumen 133 of the flexible elongate tubular member 132 to be used for inflating and deflating the respective balloons.

The distal extremity of the flexible elongate tubular member 132 can be sealed as shown in the previous embodiments. A slidable valve tube 151 is slidably mounted in the lumen 133 and is formed of a suitable plastic such as those hereinbefore described. The valve tube 151 is provided with a lumen 152 extending therethrough and opens through the distal extremity through an opening 153. The slidable valve tube 151 is formed so it forms a slidable fluid tight fit with respect to the interior surfaces with the necked down annular portions 132a, 132b and 132c.

In order to facilitate locating of the slidable valve tube 151 with respect to the openings 146, 147 and 148, the valve tube 151 is provided with a radiopaque marker 154 near the distal extremity thereof as shown in FIG. 11 which is positioned in such a manner so that when the radiopaque marker 154 is aligned with one of the radiopaque bands 136, the opening 153 is generally in communication with the respective opening of the openings 146, 147 and 148. In the position shown in FIG. 11 for the slidable valve tube 151, the second or intermediate balloon 142 will be inflated. If the radiopaque marker 154 is moved into registration with the band 136 disposed near the necked down portion 132c, the smallest balloon 141 will be inflated or deflated. Similarly, when the radiopaque marker 154 is moved into registration with the band 136 disposed near the necked down portion 132a, the largest balloon 143 can be inflated and deflated. In this manner, it can be seen that by movement of the slidable valve tube 151, the balloons 141, 142 and 143 which are coaxially mounted on the elongate tubular member 132 can be successively inflated in the manner hereinbefore described for the previous embodiments.

In FIG. 12 is shown another embodiment of an angioplasty catheter 161 incorporating the present invention which is a modification of the embodiment shown in FIG. 11. The angioplasty catheter 161 is very similar to the angioplasty catheter shown in FIG. 11. It is provided with a flexible elongate tubular member 132 having a lumen or passageway 133 therein which is provided with openings 146, 147 and 148 which establish communication between the passageway 133 and the interior of the coaxially mounted balloons 141, 142 and 143 mounted on the distal extremity of the flexible elongate member 132 in the manner hereinbefore described in conjunction with FIG. 11. However, rather than providing the tubular member 132 with necked down portions 132a, 132b and 132c, in the embodiment shown in FIG. 12 radiopaque bands 162 formed of a suitable material such as platinum are disposed within the passageway 133 and are secured to the interior wall forming the passageway 133 of the flexible elongate tubular member 132 in spaced apart positions corresponding to the positions in which the bands 136 were provided in the necked down portions 132a, 132b and 132c in FIG. 11. The slidable valve tube 151 which has a lumen 152 therein is in slidable engagement with the bands 162 to form fluid-tight seals with respect thereto. It is also provided with a radiopaque band 154.

By positioning of the slidable valve tube 151 in the manner hereinbefore described, it can be seen that the coaxially mounted balloons 141, 142 and 143 can be selectively inflated and deflated in accordance with the present invention. In the embodiment of the invention shown in FIG. 11, the distal extremity of the tubular member 132 is sealed. In the embodiment of the angioplasty catheter shown in FIG. 12, the distal extremity is rounded and is provided with a passage 166 therein which is provided within a tubular member 167 that extends through the proximal extremity of the catheter through the flow passage 152 provided in the slidable valve tube 151 so that the catheter 161 shown in FIG. 12 can be utilized in conjunction with a guide wire 168 to facilitate positioning of the catheter 161 in a vessel in a manner well known to those skilled in the art.

From the foregoing it can be seen that there has been provided an angioplasty catheter with multiple balloons that are coaxially mounted on the distal extremity permitting the physician or surgeon to utilize various sizes of balloons during an angioplasty procedure without the necessity of removing the catheter from the vessel. Each of the balloons can be independently inflated and deflated while utilizing only a single inflation/deflation lumen in the catheter.

What is claimed is:

1. An angioplasty catheter comprising a flexible elongate tubular member having proximal and distal extremities and having a lumen therein extending from the proximal extremity to the distal extremity, at least first and second balloons carried by said distal extremity and being coaxially disposed with respect to each other on the distal extremity of the flexible elongate tubular member and means carried by the flexible elongate tubular member for inflating said first and second balloons in succession, said means carried by the flexible elongate tubular member for inflating said first and second balloons including a first opening in the flexible elongate tubular member establishing communication with the lumen in the flexible elongate tubular member and the interior of the first balloon, a second opening formed in the flexible elongate tubular member and establishing communication between the lumen and the interior of the second balloon, means for supplying a fluid under pressure to the lumen in the flexible elongate tubular member and a valve tube having a lumen extending therethrough and movably mounted in said lumen in said flexible elongate tubular member for successively establishing communication between the first and second openings in the flexible elongate member and the first and second balloons so that said first and second balloons can be inflated and deflated independently of each other.

2. A catheter as in claim 1 wherein said valve tube is provided with proximal and distal extremities with the distal extremity being sealed and with the proximal extremity being in communication with the lumen in the flexible elongate tubular member.

3. A catheter as in claim 2 wherein said valve tube is provided with at least one opening wherein said one opening being adapted to be moved into registration with the openings in the flexible elongate tubular member by movement axially of the flexible elongate tubular member so that the opening in the valve tube can be selectively moved into registration one at a time with the first and second openings in the flexible elongate tubular member.

4. A catheter as in claim 3 wherein the distal extremity of said valve tube is formed of an elastic material so that when fluid under pressure is supplied to the lumen in the valve tube the valve tube is moved into sealing engagement with the flexible elongate tubular member to form a fluid-tight seal therewith.

5. A catheter as in claim 1 further including a handle mounted on the proximal extremity of the flexible elongate tubular member and a knob carried by the handle engaging the valve tube for causing movement of the valve tube.

6. A catheter as in claim 5 further including adjustable sealing means carried by the proximal extremity of the valve tube to form a fluid-tight seal between the valve tube and the handle.

7. A catheter as in claim 6 wherein said handle is provided with a chamber and means coupled to the handle and adapted to receive fluid under pressure for introduction into the chamber, said valve tube being mounted in said chamber for movement therein and means carried by the valve tube for establishing communication between the chamber and the valve tube.

8. A catheter as in claim 6 wherein said handle has an opening and wherein said adjustable sealing means is disposed in said opening in said handle.

9. A catheter as in claim 5 further including indicia carried by said knob, additional indicia carried by said handle for giving indication of the location of the distal extremity of the valve tube to indicate which of the first and second balloons can be inflated.

10. A catheter as in claim 5 wherein said handle is provided with a cutout and wherein said knob is disposed in said cutout.

11. A catheter as in claim 1 wherein the openings in the flexible elongate tubular member are offset circumferentially and wherein the valve tube is provided with first and second openings therein which are offset circumferentially with respect to each other the same distance that the openings in the flexible elongate tubular member are offset whereby upon rotation of the valve tube the balloons can be separately and independently inflated and deflated.

12. A catheter as in claim 1 wherein said valve tube is provided with a plurality of perforations establishing communication between the lumen in the valve tube and the exterior of the valve tube so that as the valve tube is moved the plurality of perforation in the valve tube can be brought into registration sequentially with the openings in the flexible elongate tubular member so that the first and second balloons can be independently and separately inflated and deflated.

13. A catheter as in claim 1 wherein said valve tube is provided with a plurality of perforations extending circumferentially about the valve tube and opening into the lumen in the valve tube to the exterior of the valve tube.

14. A catheter as in claim 1 for use with a guide wire further including a guide wire tubular member having proximal and distal extremities and having a lumen extending from the proximal extremity to the distal extremity, means securing the distal extremity of the guide wire tubular member to the distal extremity of the flexible elongate tubular member and means for securing the proximal extremity of the guide wire tubular member so that it is adapted to receive a guide wire and means surrounding the proximal extremity of the guide wire tubular member to prevent inflation fluid under pressure from entering into the lumen of the guide wire tubular member.

15. A catheter as in claim 14 wherein said valve tube is provided with a slot therein in which the guide wire tubular member is disposed and permitting axial movement of the valve tube.

16. A catheter as in claim 14 wherein said proximal extremity of the guide wire tubular member extends through the chamber and is secured to the handle.

17. A catheter as in claim 14 wherein the proximal extremity of the guide wire tubular member exits through the distal extremity of the flexible elongate tubular member to facilitate a rapid exchange.

* * * * *